United States Patent [19]
Jinotti

[11] Patent Number: 4,595,005
[45] Date of Patent: Jun. 17, 1986

[54] DUAL-PURPOSE CATHETER

[76] Inventor: Walter J. Jinotti, 10 Scott St., New Brunswick, N.J. 08903

[21] Appl. No.: 577,986

[22] Filed: Feb. 8, 1984

[51] Int. Cl.⁴ ............................................. A61M 16/00
[52] U.S. Cl. .......................... 128/205.24; 128/207.14; 128/207.16; 604/32; 604/248; 604/118
[58] Field of Search ...................... 128/205.24, 204.18, 128/207.16, 205.21, 204.25, 207.14, 207.15, 200.26; 604/32, 248, 118, 119, DIG. 9, 33; 137/625.21, 625.24

[56]  References Cited

U.S. PATENT DOCUMENTS

| 3,788,326 | 1/1974 | Jacobs | 128/207.15 |
| 4,036,210 | 7/1977 | Campbell et al. | 128/207.16 |
| 4,193,406 | 3/1980 | Jinotti | 128/205.24 |

FOREIGN PATENT DOCUMENTS

| 152622 | 10/1937 | Austria | 128/205.24 |
| 349387 | 3/1922 | Fed. Rep. of Germany | 137/625.21 |
| 545218 | 2/1932 | Fed. Rep. of Germany | 604/32 |

OTHER PUBLICATIONS

Arhelger, "The Advantages of Tracheotomy and the Use of a New Tracheal Tube in the Management of Intratracheal Aspiration", Surgery, vol. 29, No. 2, pp. 260–266, Feb. 1951.

Primary Examiner—Henry J. Recla
Attorney, Agent, or Firm—Robert A. Green

[57] ABSTRACT

A dual-purpose catheter for performing suction or oxygen feed on a patient including two cylindrical bodies rotatably coupled together and held together by a spring which is biased to hold the bodies in a first position with respect to each other but permits rotation to a second position. One body includes first and second tubes which can be coupled to a source of suction or a source of oxygen, and the other body includes means for receiving said tubes in a tight fit and tube means for coupling either suction or oxygen to the patient, depending on the rotation state of the two bodies with respect to each other.

18 Claims, 6 Drawing Figures

DUAL-PURPOSE CATHETER

BACKGROUND OF THE INVENTION

The present invention relates to a catheter which can be inserted in the body and can provide suction or oxygen as desired by the operator of the catheter. U.S. Pat. No. 4,193,406 of Walter J. Jinotti shows one form of suction-oxygen catheter which operates satisfactorily; however, the apparatus shown does not readily lend itself to mass production and is larger than is desired. It is also somewhat inconvenient to operate the catheter to switch from suction operation to oxygen feed.

The present invention provides a suction oxygen catheter which is small, easy to assemble and operate, and is easy to mass produce.

DESCRIPTION OF THE DRAWINGS

FIG. 3 is an elevational view of the patient end of the catheter valve body of the invention;

FIG. 4 is an elevational view of the end of the catheter valve body of the invention to which an oxygen source and suction source are connected;

FIG. 6 is a sectional view of flexible tubing used with the catheter of the invention.

DESCRIPTION OF THE INVENTION

Figure 1:
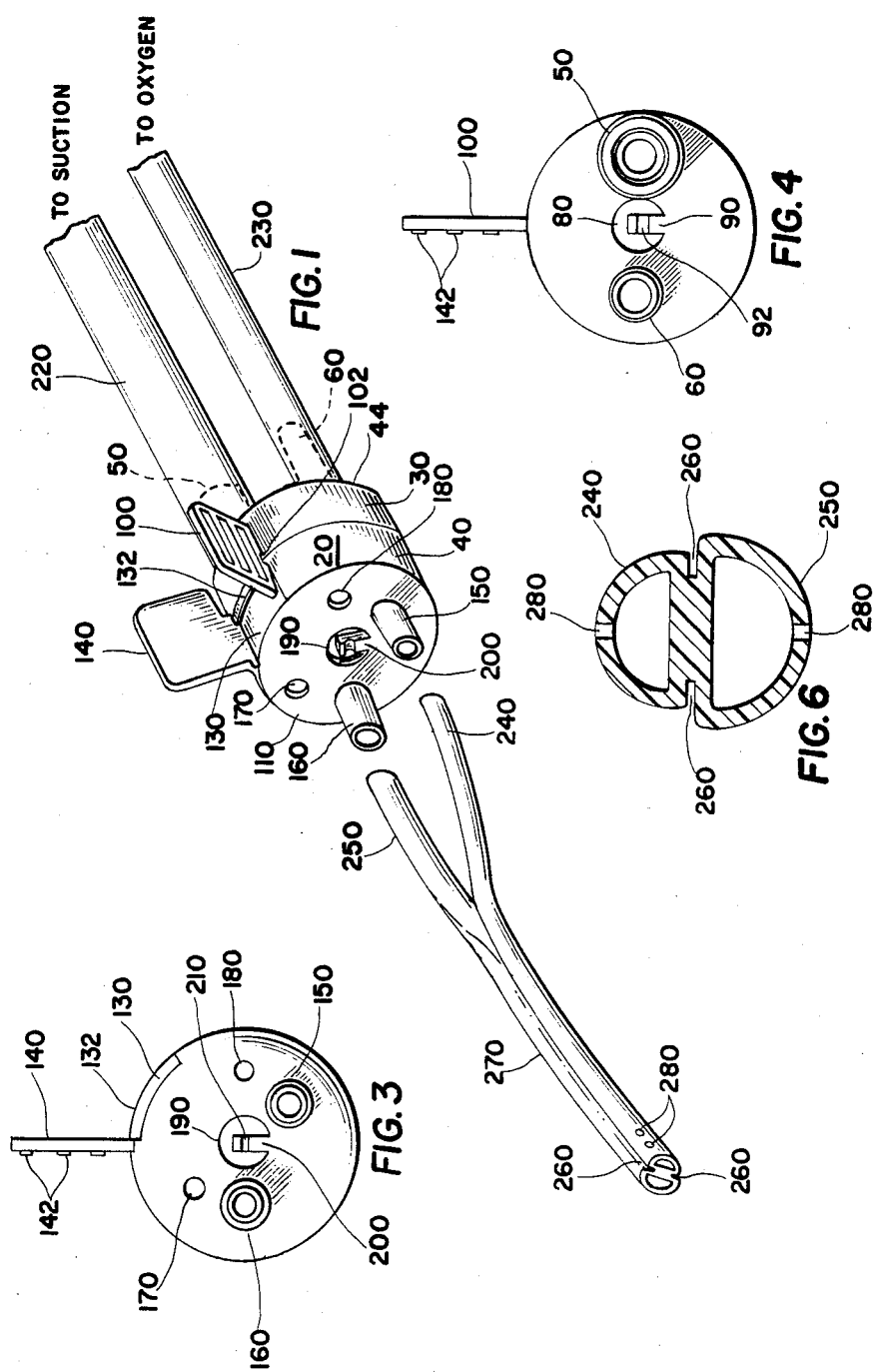
FIG. 1 is a perspective view of the catheter of the invention.

The dual purpose catheter of the invention 10 includes a valve control mechanism 20 of a synthetic resinous material comprising two bodies 30 and 40 having circular cross-sections and rotatably coupled together. One body 30 includes a flat rear wall 44, through which first and second integral tubes 50 and 60 extend so that the two tubes lie inside and outside the body and thus inside the valve mechanism. The inner ends 51 and 61 of tubes 50 and 60 are as smooth as possible for a purpose to be described. Tube 50 is used for connection to a suction source, and tube 60 for connection to an oxygen supply, and the suction tube 50 is preferably of larger diameter. A portion 70 of the inner wall of the body 30 (FIG. 2) near rear wall 44 is thickened or is of reduced inside diameter to provide an annular ledge 74 which acts as a stop for the leading end of body 40 when the two are assembled. The rear wall 44 of the body 30 also has a central hole 80 and a notched tab 90 which is formed integral with the body 30 and extends partly across the hole 80. The tab 90 has notch or depression 92 across its outer surface.

An operating finger tab 100 extends generally perpendicularly from the outer surface of the body 30 for manipulation by the operator of the catheter. The lower edge of tab 100 has a notch 102 for a purpose to be described.

The second body 40 includes a rear wall 110, whose inner surface 112 is as smooth as possible, for a purpose to be described. The annular outer wall 120 of body 40 has a portion 122 of reduced thickness or smaller outside diameter at its leading end for insertion into body 30. Also, the outer surface of the thicker portion 124 is provided with a region 130 of reduced thickness (FIG. 1) having a ledge 132 (FIGS. 1 and 2) where it joins the portion 122 of reduced thickness. An integral operating finger tab 140 extends generally perpendicularly from the thicker annular wall portion at one end of the portion 130 of reduced thickness.

Figure 2:
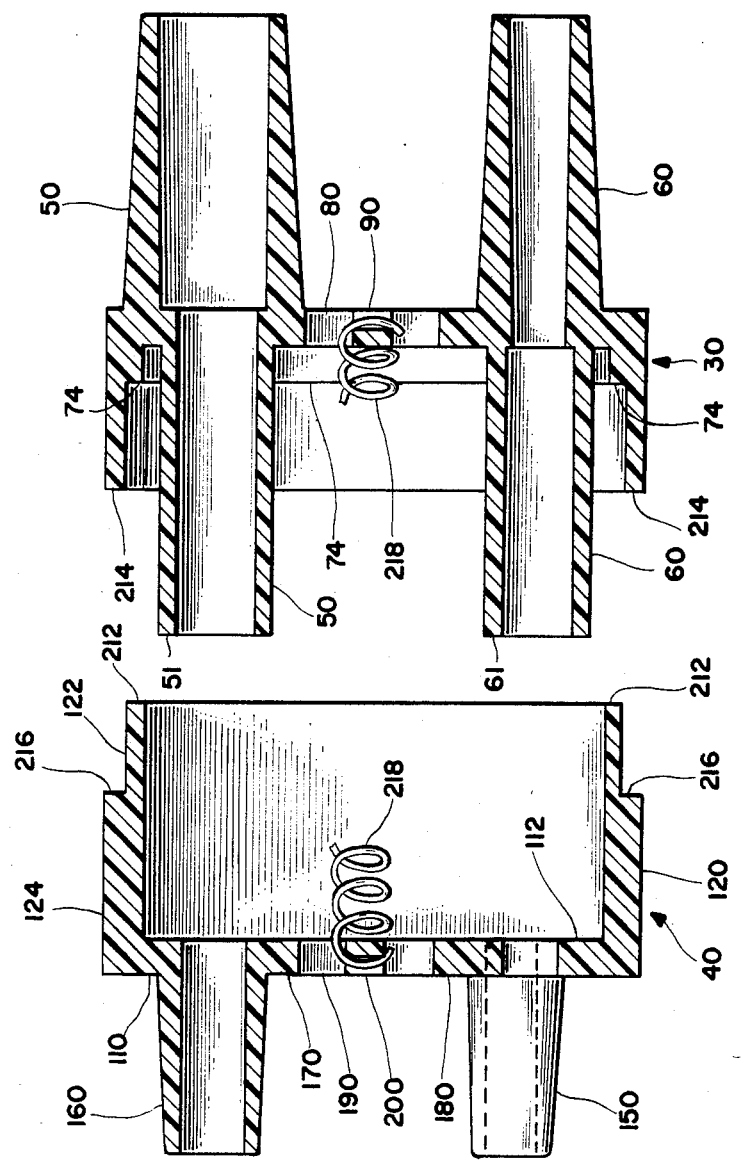
FIG. 2 is a sectional exploded view of the invention.

The finger tabs 100 and 140 are provided with roughened strips 142 on their outer opposite faces, shown only in FIGS. 2, 3, and 4, to facilitate their manipulation by the user of the catheter.

Two tubes 150 and 160 extend away from the wall 110, one 150 for oxygen and one 160 for suction. The two tubes 150 and 160 communicate with the inside of the body 40 through holes 152 and 162 in the rear wall 110. The rear wall 110 also has two holes 170 and 180 located on the same circumference as the two tubes 150 and 160, and a central opening 190. A small integral tab 200 having a notch 210 extends part way across the opening 190.

When the two bodies 30 and 40 are put together, the thin annular wall 122 of the body 40 fits snugly into the opening in body 30, and the leading end 212 butts up against the ledge 74. Similarly, the leading end 214 of body 30 butts up against ledge 216 where wall 122 meets wall 124 of the body 40. Also, the inner ends 51 and 61 of tubes 50 and 60 form a tight fit against the inner surface 112 of rear wall 110 of body 40 to provide an essentially leak-proof coupling between body 30 and body 40. When the bodies 30 and 40 are put together, the finger tab 100 slips over the rim 132, and the notch 102 in the lower surface thereof engages and locks in on the rim.

The two bodies 30 and 40 are held together securely and tightly by means of a helical spring 218 which is secured at its ends in the notches 92 and 210 in the tabs 90 and 200. In attaching the spring 218, with the two bodies 30 and 40 loosely coupled together, one end of the spring is shaped like a hook and is secured to notch 92, and, with the other end grasped by a hooked instrument, the spring is rotated to bias it, and then its other end, which is also shaped like a hook, is set in notch 210 in tab 200, and the bodies are locked together. The spring holds bodies 30 and 40 tightly together with the inner portions 51 and 61 of tubes 50 and 60 snug against the inner surface 112 of end wall 110. The bias set into the spring serves to keep the bodies 30 and 40 rotated so that the finger tabs 100 and 140 are at their maximum distance apart. With this orientation of the bodies, the oxygen tube 60 is aligned with the oxygen feed tube 150 through its hole 152 in wall 110, and the suction tube 50 is aligned with hole 170 and the ambient atmosphere. When the tabs 100 and 140 are squeezed together, the suction tube 50 is aligned with suction tube 160 through its hole 162 in the wall 110, and the oxygen tube 60 is aligned with the hole 180 and the ambient atmosphere.

The tube 50 is connected by flexible plastic tubing 220 to a source of suction (not shown), and the tube 60 is similarly connected by tubing 230 to an oxygen source (not shown).

According to the invention, the oxygen and suction tubes 150 and 160, the patient side of the valve mechanism, are connected to plastic tubes 240 and 250, respectively, which are threaded over the tubes 150 and 160 or are inserted into the tubes and are cemented therein. The oxygen tube 240 is of smaller diameter than the suction tube 250. The tubes 240 and 250 are manufactured as an integral unit, and they preferably have generally semicircular cross sections with the flat portions of the tubes adjacent to each other (FIG. 6). The tubes 240 and 250 are separated a small amount, at one end, to permit them to be secured to tubes 150 and 160. The unitary assembly of plastic tubes 240 and 250 is provided with well-defined grooves 260 between them (FIGS. 1 and 6). The tube assembly also preferably has a curvature 270 built into it when it is manufactured. The patient end of the oxygen and suction tubes also have several small holes 280 at their ends to assist them in performing their functions.

When the catheter 10 is used, both the built-in curvature 270 of the assembly of tubes 240 and 250 and the difference in the diameters of the tubes combine to impart controllability of the assembly by the operator, and permit easy guidance of the patient ends of the tubes into the throat and into the left or right lung. In addition, as the tubing is moved and rotated, the grooves 260 in the tubing act as a rake and loosen mucus which can be removed by the suction.

In using the apparatus, the finger tabs 100 and 140 and all of the parts are set so that suction force passes from the tube 250 and tube 160 through the valve 20 and out through the tube 220. At this time, oxygen flows through tubing 230 and tube 60 and out of the hole 180 to the atmosphere. After a suitable time interval of suctioning, the tabs 100 and 140 are pressed together to align the oxygen tubes 60 and 150 and to align the suction tube 50 with the hole 170 to the atmosphere, and oxygen is administered. After a while, the tabs are manipulated and oxygen is discontinued, and suction is applied.

Figure 5:
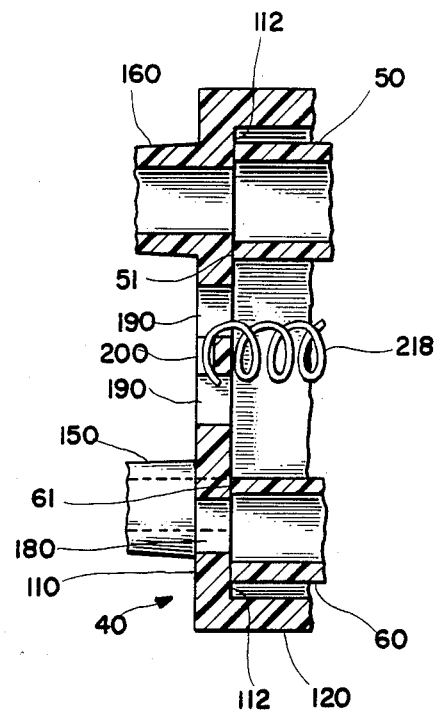
FIG. 5 is a sectional view of a portion of the catheter of the invention showing the relationship of certain parts when the catheter is assembled.

It should be understood that the drawings, and especially FIGS. 2 and 5, are drawn, in general, to make the invention clear, not to be dimensionally correct and not to show all of the parts in their exact location.

What is claimed:
1. A dual-purpose catheter comprising
   a valve mechanism including a first end which is adapted to be coupled to a patient and a second end which is adapted to be coupled to a source of oxygen and a source of suction,
   a suction tube and an oxygen tube extending from said second end of said valve mechanism and adapted to be connected to a source of suction and a source of oxygen, respectively,
   a unitary two-part tube assembly including a first flexible tube and a second flexible tube coupled to the patient end of said valve mechanism, said first and second flexible tubes having patient ends remote from said valve mechanism,
   said first and second tubes having flat wall portions along which said first and second tubes are secured together at the patient ends thereof, said wall portions of said first and second tubes facing each other and being parallel to each other,
   said wall portions having first and second ends which are left and right ends, said left ends facing each other and said right ends facing each other,
   means securing portions of said wall portions together but not securing together said wall portions at their facing left ends and right ends so that a space is present between the facing left ends and the facing right ends of said wall portions, the ends of said wall portions and the spaces between them forming generally U-shaped grooves,
   said means comprising a thickening of said wall portions, said thickening being integral with said wall portions,
   the ends of said wall portions and the spaces between the facing left and right ends thereof being able to engage and dislodge mucus which is present in the oral and tracheal passages of a patient when said unitary tube assembly is inserted into a patient, and
   operating means in said valve mechanism for coupling together either said suction tube and one of said flexible tubes or said oxygen tube and the other flexible tube.

2. A dual purpose catheter comprising
   a valve mechanism including a patient end and an inlet end for suction and oxygen and including
   a first cylindrical body and a second cylindrical body coupled together so that they can rotate with respect to each other, said first body including a suction tube and an oxygen tube which extend from inside the body to outside the body for connection outisde the body, the suction tube being adapted to be connected to a source of suction and oxygen tube being adapted to be connected to a source of oxygen,
   said second body including a rear wall having first and second holes which communicate with first and second tubes which extend away from the outer surface of said rear wall for coupling to a patient for either suction or oxygen feed, the portions of said oxygen and suction tubes inside said first body being adapted to form a tight fit with said first and second holes in said rear wall of said body and with said rear wall of said body, said oxygen and suction tubes extending up to and forming a tight fit with said rear wall,
   the rear wall of said second body also including two auxiliary holes which go to air,
   the parts of said valve mechanism being so arranged that, in operation thereof one or the other of said tubes forms a tight fit with said rear wall in alignment with its hole to couple either suction or oxygen to a patient through its hole, the tube which is not aligned with its hole being aligned with one of said auxiliary holes,
   a spring coupled at its ends to each of said bodies to hold said two bodies together, and
   finger operated means on said bodies for rotating said bodies to cause a selected alignment of either said suction tube with its hole or said oxygen tube with its hole.

3. The catheter defined in claim 2 and said spring biasis said first and second bodies so that said finger operating means are normally held apart.

4. The catheter defined in claim 3 wherein said first and second tubes have a semi-circular cross-section.

5. The catheter defined in claim 3 wherein said first and second tubes have a semi-circular cross-section and a flat wall portion, the flat wall portion of each tube comprising a diameter of the semi-circle defined by the tube, said first and second tubes being secured together along their flat wall portions.

6. The catheter defined in claim 3 wherein said tubes have different diameters.

7. The catheter defined in claim 3 wherein said tubes have different lengths and their outlet ends are offset from each other.

8. The appratus defined in claim 2 wherein said first and second tubes have different diameters.

9. A dual purpose catheter comprising
   a valve mechanism including a patient end and an inlet end,
   a suction tube connected to the inlet end of said valve mechanism, an oxygen tube connected to the inlet end of said valve mechanism, and a unitary, two-part including a first tube and a second tube connected to the patient end of said valve mechanism, said first and second tubes having free ends to be inserted into a patient, one for feeding oxygen and one for suction, each of said first and second tubes having a flat wall portion, the first and second tubes being secured together along their flat wall portions along portions of their lengths, beginning at their free ends, said valve mechanism including first and second rotatable members, coupled together and rotatable with respect to each other, said first member including a wall on the patient side of said valve mechanism, said wall having a suction hole, an oxygen hole and a pair of auxiliary holes with said suction tube being secured to the outer surface of said wall in alignment with said suction hole and said oxygen tube being secured to the outer surface of said wall in alignment with said oxygen hole, said second member including an external suction tube for connection to a source of suction and an external oxygen tube for connection to a source of oxygen, an internal suction tube aligned with and communicating with said external suction tube and an internal oxygen tube aligned with and communicating with said internal oxygen tube, said internal suction tube and internal oxygen tube extending toward said wall of said first member and forming a tight fit with said wall, the parts being arranged so that, as said first and second members are rotated with respect to each other, either said internal oxygen tube is aligned with said oxygen hole and can feed oxygen to a patient or said internal suction tube is aligned with said suction hole and can feed suction to a patient, the internal tube which is not aligned with its hole being aligned with one of said auxiliary holes.

10. The catheter defined in claim 9 wherein said first and second tubes have different diameters to facilitate control of said two-part tube as it is inserted into a patient.

11. The catheter defined in claim 9 wherein said first and second tubes have a semi-circular cross-section.

12. The catheter defined in claim 9 wherein said first and second tubes have a semi-circular cross-section, the flat wall portion of each tube comprising a diameter of the semi-circle defined by the tube.

13. The catheter defined in claim 9 wherein said tubes have different lengths and their outlet ends are offset from each other.

14. A dual-purpose catheter comprising a valve mechanism including a patient end and an inlet end, a suction tube connected to the inlet end of said valve mechanism, an oxygen tube connected to the inlet end of said valve mechanism, and a unitary two-part tube assembly including a first patient tube and a second patient tube connected to the patient end of said valve mechanism, said first and second patient tubes each having a valve end coupled to said valve mechanism and a patient end remote from said valve mechanism, said first and second tubes having different diameters, said first and second tubes having, at their patient ends, flat wall portions along which they are secured together along a portion of their lengths at their patient ends, the different diameters of said first and second tubes permitting them to be controllable guided as they are inserted into a patient, said valve mechanism including first and second rotatable members coupled together and rotatable with respect to each other, said first member including a wall on the patient side of said valve mechanism, said wall having a suction hole, an oxygen hole and a pair auxiliary holes with said suction tube secured to the outer surface of said wall in alignment with said suction hole and said oxygen tube secured to the outer surface of said wall in alignment with said oxygen hole, said second member including an external suction tube for connection to a source of suction and an external oxygen tube for connection to a source of oxygen, an internal suction tube aligned with and communicating with said external suction tube and an internal oxygen tube aligned with and communicating with said internal oxygen tube, said internal suction tube and internal oxygen tube extending toward said wall of said first member and forming a tight fit therewith and positioned so that, as said first and second members are rotated with respect to each other, either said internal oxygen tube is aligned with said oxygen hole and can feed oxygen to a patient or said internal suction tube is aligned with said suction hole and can feed suction to a patient, the internal suction or oxygen tube which is not aligned with its hole being aligned with one of said auxiliary holes.

15. The catheter defined in claim 14 wherein said first and second tubes have a semi-circular cross-section.

16. The catheter defined in claim 14 wherein said first and second tubes have a semi-circular cross-section, the falt wall portion of each tube comprising a diameter of the semi-circle defined by the tube.

17. The catheter defined in claim 14 wherein said tubes have different diameters.

18. The catheter defined in claim 14 wherein said tubes have different lengths and their outlet ends are offset from each other.

* * * * *